US009309128B2

(12) United States Patent
Kennedy et al.

(10) Patent No.: US 9,309,128 B2
(45) Date of Patent: Apr. 12, 2016

(54) ZINC OXIDE NANOSTRUCTURES AND SENSORS USING ZINC OXIDE NANOSTRUCTURES

(75) Inventors: John Vedamuthu Kennedy, Lower Hutt (NZ); Richard John Futter, Lower Hutt (NZ); Fang Fang, Lower Hutt (NZ); Andreas Markwitz, Lower Hutt (NZ)

(73) Assignee: INSTITUTE OF GEOLOGICAL AND NUCLEAR SCIENCES LIMITED, Gracefield, Lower Hutt (NZ)

( * ) Notice: Subject to any disclaimer, the term of this patent is extended or adjusted under 35 U.S.C. 154(b) by 1188 days.

(21) Appl. No.: 13/264,225

(22) PCT Filed: Apr. 14, 2010

(86) PCT No.: PCT/NZ2010/000068
§ 371 (c)(1),
(2), (4) Date: Jan. 3, 2012

(87) PCT Pub. No.: WO2010/120196
PCT Pub. Date: Oct. 21, 2010

(65) Prior Publication Data
US 2012/0091451 A1    Apr. 19, 2012

(30) Foreign Application Priority Data

Apr. 14, 2009 (NZ) ........................ 576207

(51) Int. Cl.
*C01G 9/03* (2006.01)
*B82Y 30/00* (2011.01)
(Continued)

(52) U.S. Cl.
CPC . *C01G 9/03* (2013.01); *B82Y 30/00* (2013.01); *C04B 35/453* (2013.01);
(Continued)

(58) Field of Classification Search
CPC combination set(s) only.
See application file for complete search history.

(56) References Cited

U.S. PATENT DOCUMENTS

| 7,192,802 B2 | 3/2007 | Stecker et al. |
| 7,199,029 B2 | 4/2007 | Conley, Jr. et al. |

(Continued)

FOREIGN PATENT DOCUMENTS

| CN | 1834017 | 9/2006 |
| JP | 2005-213067 | 8/2005 |

(Continued)

OTHER PUBLICATIONS

Keider et al. Increasing the length of single-wall carbon nanotubes in a magnetically enhanced art discharge App. Phy. Lett. 92 (2008) 043129 (pp. 1-3).*

(Continued)

*Primary Examiner* — Duy Deo
*Assistant Examiner* — Erin Bergner
(74) *Attorney, Agent, or Firm* — Dann, Dorfman, Herrell and Skillman, P.C.

(57) ABSTRACT

A method for preparing zinc oxide nanostructures using arc discharge is disclosed. The method comprises the provision of an anode and a cathode in an arc discharge chamber. Current is supplied to the anode and the cathode to establish an arc discharge between the cathode and the anode to vaporize the anode and produce zinc oxide nanostructures. Contemplated is the use of the zinc oxide nanostructures to produce components that have applications in, for example, optoelectronics, energy storage devices, field emission devices, and sensors such as UV photosensors, gas sensors and humidity sensors. Disclosed is a gas sensor and method for its production, where said method comprises the provision of a sensor substrate comprising a conducting thin film at least partially covering at least two regions on at least one surface of a sensor substrate material to define a gap in the conducting thin film, the application of a mixture of zinc oxide nanostructures and a non-ionic polymer to at least a portion of the gap in the conducting thin film to thereby bridge the gap. Optionally contemplated is a step of annealing the mixture of zinc oxide nanostructures and non-ionic polymer applied to said sensor substrate to produce the sensor component.

18 Claims, 8 Drawing Sheets

(51) Int. Cl.
*C04B 35/453* (2006.01)
*C04B 35/622* (2006.01)
*C04B 35/626* (2006.01)
*G01N 33/00* (2006.01)

(52) U.S. Cl.
CPC ...... *C04B 35/6268* (2013.01); *C04B 35/62231* (2013.01); *C01P 2002/54* (2013.01); *C01P 2002/72* (2013.01); *C01P 2002/76* (2013.01); *C01P 2004/03* (2013.01); *C01P 2004/16* (2013.01); *C01P 2004/54* (2013.01); *C01P 2006/40* (2013.01); *C01P 2006/60* (2013.01); *C04B 2235/3279* (2013.01); *C04B 2235/3284* (2013.01); *C04B 2235/526* (2013.01); *C04B 2235/5264* (2013.01); *G01N 33/0027* (2013.01)

(56) References Cited

U.S. PATENT DOCUMENTS

| | | | |
|---|---|---|---|
| 7,220,310 | B2 | 5/2007 | Wang et al. |
| 7,303,631 | B2 | 12/2007 | Conley, Jr. et al. |
| 7,601,324 | B1 | 10/2009 | Al-Quraishi |
| 2006/0237690 | A1* | 10/2006 | Tsuji et al. ............ 252/301.6 R |
| 2006/0240588 | A1 | 10/2006 | Conley, Jr. et al. |
| 2006/0249384 | A1 | 11/2006 | Kim et al. |
| 2006/0254501 | A1 | 11/2006 | Wang et al. |
| 2006/0292777 | A1 | 12/2006 | Dunbar |
| 2007/0249747 | A1 | 10/2007 | Tsuji et al. |
| 2007/0284573 | A1 | 12/2007 | Tseng et al. |

FOREIGN PATENT DOCUMENTS

| | | |
|---|---|---|
| JP | 2009-021102 | 1/2009 |
| WO | 2005/054869 | 6/2005 |
| WO | 2006/071199 | 7/2006 |

OTHER PUBLICATIONS

E. Monroy et al., "Wide-bandgap semiconductor ultraviolet photodetectors," Sennicond. Sci. Technol. 18 (2003), pp. R33-R51.
Yongsheng Zhang et al., "Zinc oxide nanorod and nanowire for humidity sensor," Applied Surface Science, 242 (2005), pp. 212-217.
V.V. Pokropivny et al., "Synthesis and Growth Mechanism of Zinc Oxide Nanostructures in Arc Discharge," Technical Physics Letters, 2007, vol. 33, No. 1, pp. 44-47.
F. Fang et al., "UV and humidity sensing properties of ZnO nanorods prepared by the arc discharge method," Nanotechnology, 20 (2009), pp. 1-7.
G.P. Zhu et al., "Zinc Oxide Nanorods Grown by Arc Discharge," Journal of Electronic Materials, vol. 36, No. 4, 2007, pp. 494-497.
Zhong Lin Wang, "Nanostructures of zinc oxide," materialstoday, Jun. 2004, pp. 26-33.
IP Australia Patent Examination Report, Pat. Appln. No. 2010237071, Apr. 12, 2013, pp. 1-6.
IP Australia Patent Examination Report, Pat. Appln. No. 2013201933, Apr. 12, 2013, pp. 1-6.
Intellectual Property Office of New Zealand Examination Report, Pat. Appln. No. 576207, Apr. 20, 2010, pp. 1-2.
Intellectual Property Office of New Zealand Examination Report, Pat. Appln. No. 595717, Oct. 13, 2011, pp. 1-3.
Intellectual Property Office of New Zealand Examination Report, Pat. Appln. No. 609155, Apr. 17, 2013, pp. 1-2.
N. Koprinarov et al., Synthesis of Si and ZnO nanowires and whiskers by arc discharge, Journal of Optoelectronics and Advanced Materials, vol. 11, No. 9, Sep. 2009, pp. 1304-1307.
Bulgarian Academy of Sciences Instutute of Solid State Physics, 15th International School on Condensed Matter Physics, retrieved from Internet Aug. 6, 2010, http://www.issp.bas.bg/ISCMP/iscmp2008/, published Feb. 13, 2008 as per Wayback Engine.
G.P. Zhu et al., Zinc Oxide Nanorods Grown by Arc Discharge, Journal of Electronic Materials, vol. 36, No. 4, 2007, pp. 494-497.
Xu-Feng Wu et al., ZnO Nanorods Produced by the Method of Arc Discharge, Chin. Phys. Lett., vol. 23, No. 8 (2006), pp. 2165-2168.
BASF, Luviskol VA grades, Technical Information published Nov. 1993.
PCT/NZ2010/000068, Written Opinion of the International Searching Authority, Aug. 11, 2010.

* cited by examiner (a)　　　　　　　　　　　　　(b)

ZINC OXIDE NANOSTRUCTURES AND SENSORS USING ZINC OXIDE NANOSTRUCTURES

TECHNICAL FIELD

The present invention relates to the production of zinc oxide nano structures. More particularly, but not exclusively, it relates to methods for producing zinc oxide nanostructures—especially nanorods—using arc discharge, the nanostructures produced by those methods, and the application of zinc oxide nanostructures in, for example, optoelectronic, energy storage and field emission devices, and sensors such as UV photosensors, gas sensors and humidity sensors.

BACKGROUND ART

Zinc oxide is a semiconductor with a wide band gap of 3.4 eV, which makes it transparent in visible light. Zinc oxide absorbs in the ultraviolet (UV) to blue wavelengths. Zinc oxide naturally has n-type character because of its native defects, such as oxygen vacancies or zinc interstitials. Over the last few years, thin film and bulk ZnO materials have been explored for various applications in electronics, optics and photonics.

The large surface areas of low-dimensional zinc oxide nanostructures, together with their optical and electrical properties, make them desirable for applications such as UV and humidity sensing, field mission and gas sensing. Different methods have been developed to produce one-dimensional zinc oxide nanostructures, including: vapour-liquid-solid growth; thermal evaporation; vapour phase transport; metal organic vapour phase epitaxy; chemical vapour deposition; pulsed laser deposition (PLD); laser ablation; and solution processes. The reported zinc oxide nanostructures include, for example: nanowires; nanorods; nanotubes; nanowalls; nanopropellers; nanocoral reefs; nanonetworks; and quantum wells.

These methods for producing zinc oxide nanostructures typically involve high cost and multiple processing steps. There remains a need for low cost, reproducible, large scale production techniques.

Accordingly, it is an object of the present invention to go some way to avoiding the above disadvantages and/or to at least provide the public with a useful choice.

Other objects of the invention may become apparent from the following description which is given by way of example only.

In this specification where reference has been made to patent specifications, other external documents, or other sources of information, this is generally for the purpose of providing a context for discussing the features of the invention. Unless specifically stated otherwise, reference to such external documents is not to be construed as an admission that such documents, or such sources of information, in any jurisdiction, are prior art, or form part of the common general knowledge in the art.

SUMMARY OF THE INVENTION

In a first aspect, the present invention provides a method for producing zinc oxide nanostructures, the method comprising:
  providing an anode and a cathode in an arc discharge chamber;
  supplying current to the anode and the cathode to establish an arc discharge between the cathode and the anode to vaporise the anode and produce the zinc oxide nanostructures;
  terminating the current supply to the anode and the cathode; and
  collecting the resulting zinc oxide nanostructures.

In another aspect, the present invention provides zinc oxide nanostructures produced substantially according to the above method.

In another aspect, the present invention provides zinc oxide nanostructures produced by a method comprising:
  providing an anode and a cathode in an arc discharge chamber;
  supplying current to the anode and the cathode to establish an arc discharge between the cathode and the anode to vaporise the anode and produce the zinc oxide nanostructures;
  terminating the current supply to the anode and the cathode; and
  collecting the resulting zinc oxide nanostructures.

In another aspect, the present invention provides zinc oxide nanostructures produced substantially according to the above method for use in optoelectronic, energy storage and field emission devices, and sensors.

In another aspect, the present invention provides zinc oxide nanostructures produced by a method comprising:
  providing an anode and a cathode in an arc discharge chamber;
  supplying current to the anode and the cathode to establish an arc discharge between the cathode and the anode to vaporise the anode and produce the zinc oxide nanostructures;
  terminating the current supply to the anode and the cathode; and
  collecting the resulting zinc oxide nanostructures;
for use in optoelectronic, energy storage and field emission devices, and sensors.

In another aspect, the present invention provides an optoelectronic device component comprising zinc oxide nanostructures of the invention.

In another aspect, the present invention provides an energy storage device component comprising zinc oxide nanostructures of the invention.

In another aspect, the present invention provides a field emission device component comprising zinc oxide nanostructures of the invention.

In another aspect, the present invention provides a sensor component comprising zinc oxide nanostructures of the invention.

The present invention also provides a method for producing a sensor component, the sensor component comprising zinc oxide nanostructures of the invention.

In another aspect, the present invention provides a method for producing a sensor component, the method comprising:
  providing a sensor substrate comprising a conducting thin film at least partially covering at least two regions on at least one surface of a sensor substrate material to define a gap in the conducting thin film;
  applying a mixture comprising zinc oxide nanostructures and a nonionic polymer to at least a portion of the gap in the conducting thin film and thereby bridge the gap; and
  optionally, annealing the mixture of zinc oxide nanostructures and nonionic polymer applied to the sensor substrate, to provide the sensor component.

In another aspect, the present invention provides a method for producing a sensor component, the method comprising:
  providing an anode and a cathode in an arc discharge chamber;

supplying current to the anode and the cathode to establish an arc discharge between the cathode and the anode to vaporise the anode and produce the zinc oxide nanostructures;

terminating the current supply to the anode and the cathode;

collecting the resulting zinc oxide nanostructures;

providing a sensor substrate comprising a conducting thin film at least partially covering at least two regions on at least one surface of a sensor substrate material to define a gap in the conducting thin film;

applying a mixture comprising the zinc oxide nanostructures and a nonionic polymer to at least a portion of the gap in the conducting thin film and thereby bridge the gap; and optionally, annealing the mixture of zinc oxide nanostructures and nonionic polymer applied to the sensor substrate, to provide the sensor component.

In another aspect, the present invention provides a sensor component produced substantially according to the above method.

In another aspect, the present invention provides a sensor component produced by a method comprising:

providing a sensor substrate comprising a conducting thin film at least partially covering at least two regions on at least one surface of a sensor substrate material to define a gap in the conducting thin film;

applying a mixture comprising zinc oxide nanostructures and a nonionic polymer to at least a portion of the gap in the conducting thin film and thereby bridge the gap; and optionally, annealing the mixture of zinc oxide nanostructures and nonionic polymer applied to the sensor substrate, to provide the sensor component.

In another aspect, the present invention provides a sensor component produced by a method comprising:

providing an anode and a cathode in an arc discharge chamber;

supplying current to the anode and the cathode to establish an arc discharge between the cathode and the anode to vaporise the anode and produce the zinc oxide nanostructures;

terminating the current supply to the anode and the cathode;

collecting the resulting zinc oxide nanostructures;

providing a sensor substrate comprising a conducting thin film at least partially covering at least two regions on at least one surface of a sensor substrate material to define a gap in the conducting thin film;

applying a mixture comprising the zinc oxide nanostructures and a nonionic polymer to at least a portion of the gap in the conducting thin film and thereby bridge the gap; and optionally, annealing the mixture of zinc oxide nanostructures and nonionic polymer applied to the sensor substrate, to provide the sensor component.

In another aspect, the present invention provides a sensor component comprising:

a sensor substrate comprising a conducting thin film at least partially covering at least two regions on at least one surface of a sensor substrate material to define a gap in the conducting thin film; and a mixture comprising zinc oxide nanostructures and a nonionic polymer covering at least a portion of the gap in the conducting thin film, thereby bridging the gap.

This invention may also be said broadly to consist in the parts, elements and features referred to or indicated in the specification of the application, individually or collectively, and any or all combinations of any two or more said parts, elements or features, and where specific integers are mentioned herein which have known equivalents in the art to which this invention relates, such known equivalents are deemed to be incorporated herein as if individually set forth.

As used herein the term "and/or" means "and" or "or" or both.

The term "comprising" as used in this specification means "consisting at least in part of". When interpreting each statement in this specification that includes the term "comprising", features other than that or those prefaced by the term may also be present. Related terms such as "comprise" and "comprises" are to be interpreted in the same manner.

It is intended that reference to a range of numbers disclosed herein (for example, 1 to 10) also incorporates reference to all rational numbers within that range (for example, 1, 1.1, 2, 3, 3.9, 4, 5, 6, 6.5, 7, 8, 9 and 10) and also any range of rational numbers within that range (for example, 2 to 8, 1.5 to 5.5 and 3.1 to 4.7) and, therefore, all sub-ranges of all ranges expressly disclosed herein are hereby expressly disclosed. These are only examples of what is specifically intended and all possible combinations of numerical values between the lowest value and the highest value enumerated are to be considered to be expressly stated in this application in a similar manner.

Although the present invention is broadly as defined above, those persons skilled in the art will appreciate that the invention is not limited thereto and that the invention also includes embodiments of which the following description gives examples.

BRIEF DESCRIPTION OF THE DRAWINGS

The invention will now be described with reference to the Figures in which.

DETAILED DESCRIPTION OF THE INVENTION

Figure 1:
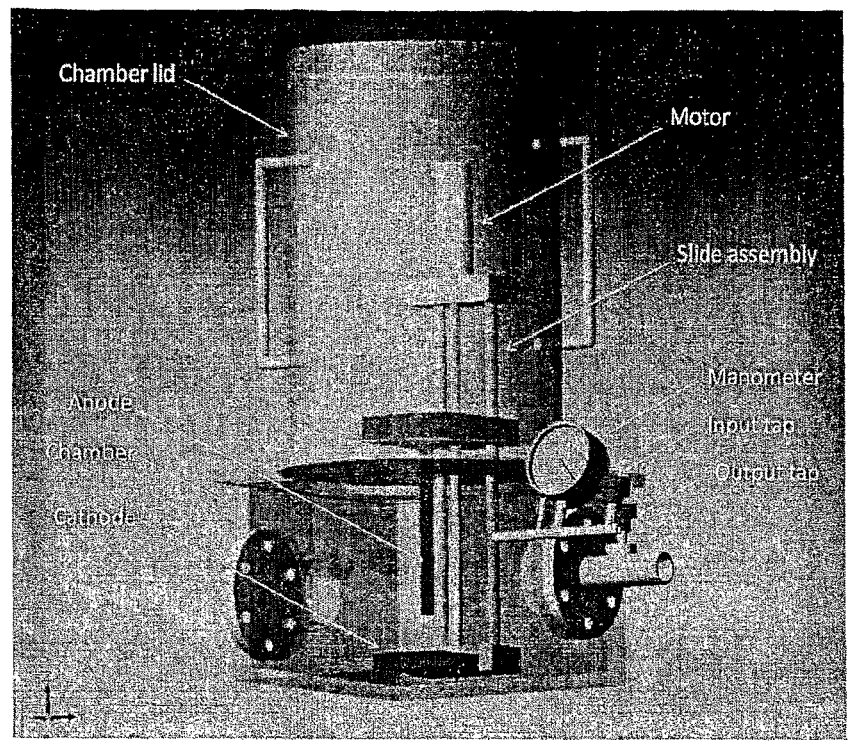
FIG. 1 is a three dimensional model of one type of arc discharge apparatus.

A method for producing zinc oxide nanostructures, especially nanorods, using arc discharge has been devised.

Accordingly, in a first aspect, the present invention provides a method for producing zinc oxide nanostructures, the method comprising:
providing an anode and a cathode in an arc discharge chamber;
supplying current to the anode and the cathode to establish an arc discharge between the cathode and the anode to vaporise the anode and produce the zinc oxide nanostructures;
terminating the current supply to the anode and the cathode; and
collecting the resulting zinc oxide nanostructures.

In one embodiment, the anode is a high purity zinc anode.

High purity zinc anodes are commercially available. In one embodiment, the zinc anode is at least 99.0% pure, preferably at least 99.9% pure, more preferably at least 99.99% pure.

In a preferred embodiment, the zinc anode is at least 99.999% pure.

In another embodiment, the anode comprises zinc and is doped with one or more metallic donor. In one embodiment, the anode is doped with one metallic donor. In another embodiment, the anode is doped with two or more metallic donors. In these embodiments, the one or more metallic donor comprises from about 0.1 atomic % to about 10 atomic % of the anode.

In one embodiment wherein the anode comprises zinc doped with one or more metallic donor, the zinc that is combined with the metallic donor is at least 99.0% pure, preferably at least 99.9% pure, more preferably at least 99.99% pure, more preferably at least 99.999% pure. Preferably, the one or more metallic donor that is combined with the zinc is at least 99.0% pure, preferably at least 99.5% pure.

In one embodiment, the one or more metallic donor is selected from the group consisting of: the noble metals (including ruthenium, rhodium, palladium, silver, osmium, iridium, platinum and gold); the magnetic metals (including iron, cobalt and nickel); and antimony.

In another embodiment, the one or more metallic donor is selected from the group consisting of: palladium; silver; platinum; gold; nickel; and antimony.

In a preferred embodiment, the metallic donor is nickel. In another preferred embodiment, the zinc anode is doped with about 2.0 atomic % nickel.

In one embodiment, the anode is a high purity zinc rod, preferably with a diameter between about 5 mm and about 15 mm.

In one embodiment, the cathode is a high purity cathode.

In one embodiment, the cathode is at least 99.0% pure, preferably at least 99.9% pure, more preferably at least 99.99% pure.

In a preferred embodiment, the cathode is at least 99.999% pure.

In a preferred embodiment, the cathode is a graphite cathode. In another preferred embodiment, the cathode is a copper cathode.

Preferably, the cathode is water-cooled. In a preferred embodiment, the cathode is a water-cooled graphite disc electrode and/or a water-cooled copper disc electrode.

In those embodiments wherein the cathode is a water-cooled copper disc, the disc is preferably about 30 mm to about 100 mm in diameter with a thickness between about 10 mm and about 25 mm. Preferred water-cooled graphite cathodes have similar dimensions.

Those persons skilled in the art will be able to select a suitable cathode without undue experimentation. The cathode must be able to withstand the conditions in the arc discharge chamber during the arc discharge. Cathodes other than those described above, for example a zinc cathode or a multielement cathode, may also be useful in the invention.

Various arc discharge apparatus are known in the art and one type is illustrated in FIG. 1. The arc discharge apparatus in FIG. 1 includes a chamber containing an anode and a cathode. The chamber is sealed with a chamber lid housing a motor and a slide assembly. The chamber is equipped with a manometer and input and output taps.

In a preferred embodiment, the cathode is arranged horizontally in the arc discharge chamber and the anode is arranged vertically. Without wishing to be bound by theory, it is thought that, in this embodiment, heat rises towards the anode, assisting the thermalisation of excited atoms and producing highly pure zinc oxide nanostructures.

In one embodiment, the distance between the anode and the cathode may be varied. For example, an electric motor may be used to control the distance between the anode and the cathode. Preferably the distance between the anode and the cathode is between about 3 mm and about 7 mm. In one embodiment, the distance between the anode and the cathode is about 5 mm.

In one embodiment, the pressure in the arc discharge chamber may be varied. For example, a rotary pump may be used in conjunction with a variable inlet gas flow to vary the pressure. Preferably, the pressure in the arc discharge chamber is between about 300 Torr (40 kPa) and about 700 Torr (93.3 kPa). In one embodiment, the pressure in the arc discharge chamber is about 400 Torr (53.3 kPa). In another embodiment, the pressure in the arc discharge chamber is about 500 Torr (66.7 kPa).

In one embodiment, the atmosphere in the arc discharge chamber comprises air. Other atmospheres may be used, for example: oxygen; and mixtures of oxygen with one or more other gas; such as argon, neon, xenon, helium and nitrogen. In another embodiment, the atmosphere in the arc discharge chamber comprises ozone or a mixture of ozone with one or more other gas, such as oxygen, argon, neon, xenon, helium and nitrogen.

In one embodiment, the atmosphere in the arc discharge chamber comprises a mixture of oxygen and/or ozone with one or more of argon, neon and xenon.

In a preferred embodiment, the atmosphere in the arc discharge chamber comprises a mixture of oxygen and argon.

The atmosphere in the arc discharge chamber will typically comprise at least about 10% oxygen. In one embodiment, the atmosphere in the arc discharge chamber comprises about 21% oxygen. In another embodiment, the atmosphere in the arc discharge chamber comprises about 25% oxygen. In another embodiment, the atmosphere in the arc discharge chamber comprises about 50% oxygen. In another embodiment, the atmosphere in the arc discharge chamber comprises about 99.5% oxygen.

In one embodiment, the atmosphere in the arc discharge chamber comprises at least about 21% oxygen, at least about 25% oxygen, at least about 50% oxygen, or at least about 99.5% oxygen.

Current may be supplied to the anode and the cathode using any conventional means.

In one embodiment, a DC power supply, such as an inverter-type TIG welder, is used. Advantageously, the positive terminal (anode) gets hotter than the negative terminal (cathode) for DC arcs.

Preferably, the current supplied to the anode and the cathode is between about 30 A and about 70 A. The resulting voltage is a function of the electrode separation and the atmosphere within the arc discharge chamber. In one embodiment, the current supplied to the anode and the cathode is about 50 A.

Typically, the arc discharge between the cathode and the anode is established for between about 10 seconds and about 50 seconds. In one embodiment, the arc discharge is established for about 20 seconds.

The current supplied to the electrodes creates a high temperature arc discharge between them. The discharge vaporises the anode material, and the vaporised material reacts with the atmosphere within the arc discharge chamber.

The zinc oxide nanostructures typically form as a white and/or yellow white powder, which adheres to the cathode and other surfaces within the arc discharge chamber. The powder may be collected by, for example, scraping it off these surfaces.

Advantageously, the zinc oxide nanostructures are typically obtained with high quality and high purity and are suitable for use without further purification.

In one embodiment, the method further comprises placing a nanostructure growth substrate in the arc discharge chamber. Preferably, the nanostructure growth substrate is placed in the arc discharge chamber before establishing the arc discharge between the cathode and the anode. In some embodiments, the nanostructure growth substrate may be placed in the arc discharge chamber during the arc discharge.

During the arc discharge, a thin film of zinc oxide nanostructures forms on at least that surface of the nanostructure growth substrate which faces the plasma. Zinc oxide nanostructures may also form on other surfaces of the nanostructure growth substrate due to scattering from the chamber walls. In this embodiment, the zinc oxide nanostructures are collected by removing the nanostructure growth substrate from the arc discharge chamber.

Preferably, the nanostructure growth substrate is placed around the cathode at a distance of about 20 mm to about 100 mm from the cathode.

In some embodiments, the nanostructure growth substrate is retained in the arc discharge chamber for multiple arc discharges to build up a thicker film of zinc oxide nano structures.

The nanostructure growth substrate must be able to withstand the conditions in the arc discharge chamber during the arc discharge without, for example, breaking down or outgassing. Suitable nanostructure growth substrates will generally be stable at temperatures up to at least about 300° C.

Suitable nanostructure growth substrates include, but are not limited to, silicon, glass and quartz.

In one embodiment, the nanostructure growth substrate is substantially planar.

The size of the nanostructure growth substrate will depend on factors such as the size of the arc discharge chamber. In one embodiment, the nanostructure growth substrate is substantially planar with dimensions of about 1 cm by about 1 cm.

Prior to being placed into the arc discharge chamber, the nanostructure growth substrate may be mechanically cleaned by, for example, spraying compressed air onto the surface:

In one embodiment, the nanostructure growth substrate comprises a plurality of individual pieces of substrate that are moved sequentially or concurrently into the arc discharge chamber and then moved out of the chamber after the zinc oxide nanostructures have been formed on the substrate.

In another aspect, the present invention provides zinc oxide nanostructures produced substantially according to the above method.

In another aspect, the present invention provides zinc oxide nanostructures produced by a method comprising:
 providing an anode and a cathode in an arc discharge chamber;
 supplying current to the anode and the cathode to establish an arc discharge between the cathode and the anode to vaporise the anode and produce the zinc oxide nanostructures;
 terminating the current supply to the anode and the cathode; and
 collecting the resulting zinc oxide nanostructures.

The zinc oxide nanostructures typically form as nanorods. Using the method of the invention, zinc oxide nanorods have been obtained with diameters between about 20 nm and about 400 nm and lengths between about 0.02 μm and about 10 μm.

In one embodiment, the zinc oxide nanorods have lengths between about 0.1 μm and about 5 μm. In another embodiment, the zinc oxide nanorods have lengths between about 0.02 μm and about 10 μm. In another embodiment, the zinc oxide nanorods have lengths between about 0.03 μm and about 0.6 μm. In another embodiment, the zinc oxide nanorods have lengths between about 0.02 μm and about 0.2 μm.

The aspect ratio of the nanorods may depend upon the oxygen partial pressure of the atmosphere in the arc discharge chamber. In one embodiment, the aspect ratio of the nanorods increases as the oxygen partial pressure increases.

The large surface areas of the zinc oxide nanostructures, together with their optical and electrical properties, make them useful for application in, for example, optoelectronic (including, but not limited to, photovoltaic), energy storage, and field emission devices, and sensors such as UV photosensors, gas sensors and humidity sensors.

Accordingly, in another aspect, the present invention provides zinc oxide nanostructures produced substantially according to the above method for use in optoelectronic, energy storage and field emission devices, and sensors. In another aspect, the present invention provides zinc oxide nanostructures produced substantially according to the above method for use in optoelectronic and field emission devices, and sensors.

In another aspect, the present invention provides zinc oxide nanostructures produced by a method comprising:
 providing an anode and a cathode in an arc discharge chamber;
 supplying current to the anode and the cathode to establish an arc discharge between the cathode and the anode to vaporise the anode and produce the zinc oxide nanostructures;
 terminating the current supply to the anode and the cathode; and
 collecting the resulting zinc oxide nanostructures;
for use in optoelectronic, energy storage and field emission devices, and sensors.

In another aspect, the present invention provides an optoelectronic device component comprising zinc oxide nanostructures of the invention.

In another aspect, the present invention provides an energy storage device component comprising zinc oxide nanostructures of the invention.

In another aspect, the present invention provides a sensor component comprising zinc oxide nanostructures of the invention.

The present invention also provides a method for producing a sensor component, the sensor component comprising zinc oxide nanostructures of the invention.

In another aspect, the present invention provides a method for producing a sensor component, the method comprising:

providing a sensor substrate comprising a conducting thin film at least partially covering at least two regions on at least one surface of a sensor substrate material to define a gap in the conducting thin film;

applying a mixture comprising zinc oxide nanostructures and a nonionic polymer to at least a portion of the gap in the conducting thin film and thereby bridge the gap; and optionally, annealing the mixture of zinc oxide nanostructures and nonionic polymer applied to the sensor substrate, to provide the sensor component.

In a preferred embodiment, the zinc oxide nanostructures are produced substantially according to the method of the first aspect.

Accordingly, in another aspect, the present invention provides a method for producing a sensor component, the method comprising:

providing an anode and a cathode in an arc discharge chamber;

supplying current to the anode and the cathode to establish an arc discharge between the cathode and the anode to vaporise the anode and produce the zinc oxide nanostructures;

terminating the current supply to the anode and the cathode;

collecting the resulting zinc oxide nanostructures;

providing a sensor substrate comprising a conducting thin film at least partially covering at least two regions on at least one surface of a sensor substrate material to define a gap in the conducting thin film;

applying a mixture comprising the zinc oxide nanostructures and a nonionic polymer to at least a portion of the gap in the conducting thin film and thereby bridge the gap; and optionally, annealing the mixture of zinc oxide nanostructures and nonionic-polymer applied to the sensor substrate, to provide the sensor component.

In one embodiment, the sensor substrate material is an electrical insulator. Suitable sensor substrate materials will generally have a resistivity of at least about $1 \times 10^{-3}$ $\Omega$m. Suitable sensor substrate materials include, but are not limited to: silicon; $SiO_2$; sapphire; glass; $Al_2O_3$; silicon nitride; silicon oxynitride; and various plastics, such as Kapton® (polyimide).

In one embodiment, the sensor substrate material essentially consists of a single material. In other embodiments, the sensor substrate material comprises a first substrate material that is coated with one or more other substrate materials.

In one embodiment, the sensor substrate material is silicon, $SiO_2$ or glass. In another embodiment, the sensor substrate material is silicon or glass. In a preferred embodiment, the sensor substrate material is silicon coated with $SiO_2$.

In one embodiment, the sensor substrate is substantially planar. In another embodiment, the sensor substrate is substantially planar with dimensions of about 1 cm by about 1 cm. In the embodiment shown in FIG. 2, the sensor substrate material is silicon coated with $SiO_2$.

Conducting thin films are known in the art. Suitable conducting thin films will generally have an electrical conductivity of at least about 100 $Sm^{-1}$. Suitable conducting thin films comprise metals, such as gold or aluminum, mixtures of metals, or other materials, such as indium tin oxide (ITO) and insulators with sufficient doping to satisfy the conductivity criterion.

Figure 2:
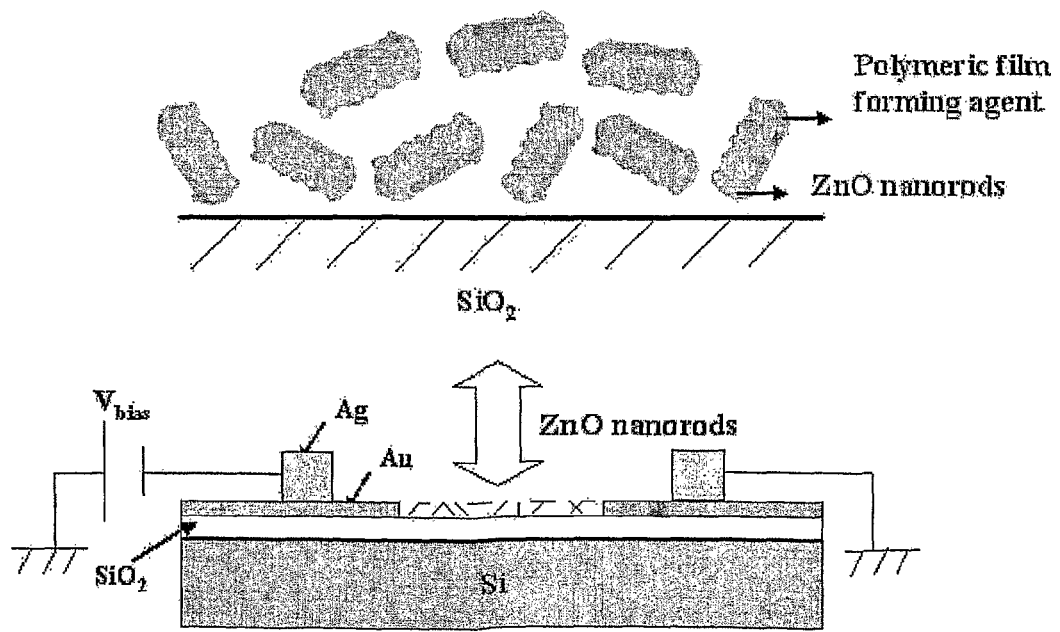
FIG. 2 is a schematic diagram of one embodiment of a sensor comprising zinc oxide nanorods.

In the embodiment shown in FIG. 2, the conducting thin film comprises gold.

Prior to application of the conducting thin film, the sensor substrate material may be mechanically cleaned by, for example, spraying compressed air onto the surface. The sensor substrate material may also be washed with a suitable solvent, such as ethanol, either with or without ultrasonication. In some embodiments, the sensor substrate material may be chemically treated before applying the conducting thin film. However, in preferred embodiments, such chemical treatment is not necessary.

The conducting thin film may be applied to the sensor substrate material using known techniques. In one embodiment, the conducting thin film is applied to the sensor substrate material using a sputter coater. However, other methods will be readily apparent to those persons skilled in the art.

The thickness of the conducting thin film is typically between about 20 nm and about 100 nm. However, in some embodiments, the thickness may be outside this range.

The zinc oxide nanostructures are mixed with a nonionic polymer. Suitable nonionic polymers include nonionic polymer surfactants and nonionic polymeric film-forming agents. Without wishing to be bound by theory, it is thought that the nonionic polymer forms a layer around each of the individual zinc oxide nanostructures, thereby reducing aggregation of the nanostructures.

In one embodiment, the nonionic polymer is selected from the group consisting of nonionic polymer surfactants; nonionic polymeric film-forming agents; and mixtures of any two or more thereof.

In one embodiment, the nonionic polymer is a nonionic polymer surfactant.

In another embodiment, the nonionic polymer is a nonionic polymeric film-forming agent. In a preferred embodiment, the nonionic polymer is a vinylpyrrolidone/vinyl acetate copolymer. Preferably, the ratio of vinylpyrrolidone:vinyl acetate in the nonionic polymer is 60:40.

One such polymer is marketed as BASF LUVISKOL® VA 64.

The nonionic polymer assists the formation of 3D networks of the zinc oxide nanostructures, without influencing the conductivity properties of the sensor component as might be expected if, for example, an ionic surfactant were used. Thus, the nonionic polymer improves the conductivity of the sensor component comprising zinc oxide nanostructures, without affecting the working mechanism of the sensor component.

In a preferred embodiment, the mixture further comprises a solvent. The solvent is generally a volatile organic solvent in which the nonionic polymer is soluble.

In one embodiment, the solvent is ethanol. Other suitable solvents include, but are not limited to: other alcohols, such as methanol, iso-propanol and butanol; halocarbons, such as dichloromethane and chloroform; ethers; such as tetrahydrofuran; esters, such as ethyl acetate; ketones, such as acetone; and acetonitrile. Mixtures of any two or more suitable solvents may also be used.

The weight ratio of zinc oxide nanostructures to nonionic polymer in the mixture is typically in the range about 1:1 to about 8:1. In those embodiments wherein the mixture further comprises a solvent, the weight ratio of zinc oxide nanostructures to nonionic polymer to solvent is typically in the range about 1:1:8 to about 8:1:8. However, weight ratios outside of this range may be used, depending on the specific nonionic polymer and solvent, if present.

In one embodiment, wherein the nonionic polymer is BASF LUVISKOL® VA 64 and the solvent is ethanol, a preferred weight ratio of zinc oxide nanostructures to nonionic polymer to solvent is 3:1:8.

In one embodiment, the mixture comprising the zinc oxide nanostructures and the nonionic polymer, together with the solvent, if present, is ultrasonicated. Ultrasonication assists in breaking up any nanostructure aggregates and dispersing the nanostructures throughout the mixture. Other conventional techniques, such as vigorous stilling, may also be effective.

In a preferred embodiment, the mixture is ultrasonicated for between about one minute and about 30 minutes at a temperature from about 10° C. to about 60° C. However, in some embodiments, the ultrasonication time and/or temperature may be outside this range depending on, for example, the boiling point of any solvent present in the mixture.

The mixture comprising the zinc oxide nanostructures and the nonionic polymer, together with the solvent, if present, is then applied to at least a portion of the gap in the conducting thin film on the sensor substrate. In the embodiment shown in FIG. 2, the conducting thin film is a gold thin film and the zinc oxide nanostructure/nonionic polymer mixture bridges a gap in the gold film.

In one embodiment, the mixture is applied by dropping the mixture onto the surface of the sensor substrate and drying in the open air to evaporate the solvent.

The amount of solvent in the mixture will affect the thickness of the resulting zinc oxide nanostructures/nonionic polymer film.

The resistivity of the zinc oxide nanostructures/nonionic polymer film is inversely proportional to the thickness of the film. In some embodiments, multiple applications of the mixture may be used to build up a thicker film.

In one embodiment, the thickness of the zinc oxide nanostructures/nonionic polymer film is from about 100 nm to about 5 μm.

Annealing the mixture of zinc oxide nanostructures and nonionic polymer applied to the sensor substrate improves the mechanical strength of the sensor component by hardening the nonionic polymer, and also improves the photoconductivity of the resulting sensor component.

Those persons skilled in the art will be able to select suitable annealing conditions without undue experimentation. In one embodiment, the mixture of zinc oxide nanostructures and nonionic polymer, applied to the sensor substrate is annealed in air at a temperature between about 50° C. and about 250° C. for between about 10 minutes and about 60 minutes. In other embodiments, annealing temperatures and/or times outside these ranges may be used. In a preferred embodiment, the Mixture of zinc oxide nanostructures and nonionic polymer applied to the sensor substrate is annealed in air at a temperature of about 200° C. for about 30 minutes.

In another aspect, the present invention provides a sensor component produced substantially according to the above method.

In another aspect, the present invention provides a sensor component produced by a method comprising:
  providing a sensor substrate comprising a conducting thin film at least partially covering at least two regions on at least one surface of a sensor substrate material to define a gap in the conducting thin film;
  applying a mixture comprising zinc oxide nanostructures and a nonionic polymer to at least a portion of the gap in the conducting thin film and thereby bridge the gap; and
  optionally, annealing the mixture of zinc oxide nanostructures and nonionic polymer applied to the sensor substrate, to provide the sensor component.

In another aspect, the present invention provides a sensor component produced by a method comprising:
  providing an anode and a cathode in an arc discharge chamber;
  supplying current to the anode and the cathode to establish an arc discharge between the cathode and the anode to vaporise the anode and produce the zinc oxide nanostructures;
  terminating the current supply to the anode and the cathode;
  collecting the resulting zinc oxide nanostructures;
  providing a sensor substrate comprising a conducting thin film at least partially covering at least two regions on at least one surface of a sensor substrate material to define a gap in the conducting thin film;
  applying a mixture comprising the zinc oxide nanostructures and a nonionic polymer to at least a portion of the gap in the conducting thin film and thereby bridge the gap; and
  optionally, annealing the mixture of zinc oxide nanostructures and nonionic polymer applied to the sensor substrate, to provide the sensor component.

In another aspect, the present invention provides a sensor component comprising:
  a sensor substrate comprising a conducting thin film at least partially covering at least two regions on at least one surface of a sensor substrate material to define a gap in the conducting thin film; and
  a mixture comprising zinc oxide nanostructures and a nonionic polymer covering at least a portion of the gap in the conducting thin film, thereby bridging the gap.

In a preferred embodiment, the zinc oxide nanostructures are produced substantially according to the method of the first aspect.

Sensors may be fabricated from the sensor components of the invention by the addition of other conventional components such as contacts, a power supply and electrical and/or optical measuring apparatus. The sensor may further include components intended to protect and extend the longevity of the mixture of zinc oxide nanostructures and nonionic polymer. For example, a quartz cover may be useful for a UV sensor and a moisture permeable mesh may be useful for a humidity sensor.

Sensors fabricated using sensor components produced according to the above method have been tested under UV illumination and also under varying relative humidity. The sensors behaved as a variable resistor, with the resistance being inversely proportional to the applied illumination or the relative humidity. Accordingly, the sensor components of the invention are useful for producing photosensors, especially for use in the UV region, and humidity sensors.

The responsivity of most commercial UV photodetectors currently available in the market is in the range of 0.1 to 0.2 A/W [E Monroy, F Omnes and F Calle *Semicond. Sci. Technol.* 18 33-51 (2003)]. Sensors fabricated using sensor components produced according to the above method have been shown to exhibit responsivities of about 0.01 to 1.0 A/W under UV (340 nm) illumination.

The sensitivity factor ($S_f$) for a humidity sensor fabricated using a sensor component produced according to the above method was calculated as $S_f = R_{7\%}/R_{95\%} = 8790$. This is higher than the sensitivity for another zinc oxide nanorod sensor ($S_f$=183) and a zinc oxide nanowire sensor ($S_f$=5442), both reported by Y S Zhang et al. [*Appl. Surf Sci.* 242 212-217 (2005)].

Accordingly, the methods of the present invention enable the fabrication of sensors comprising zinc oxide nanostructures having very good sensitivities without employing the clean room procedures typically used for inter-digitized electrode fabrication and packaging.

Electron field emission is the electric field induced emission of electrons from the surface of condensed matter into vacuum, gas, liquid or a non-metallic solid with low electrical conductivity. In contrast to thermionic electron emission, electric field induced emission of electrons does not rely on high temperature (>800° C.) for operation. As a consequence, electron field emitting materials can be termed cold cathode electron emitters. Cold cathodes have advantages over thermionic emitters such as instant turn-on, lower energy requirements and lower energy spread. Cold cathode electron emitters have potential applications that include, but are not limited to: field emission displays; vacuum fluorescent displays; plasma displays; lighting elements; microwave generation; space-vehicle neutralization; and X-ray generation. The electrons are emitted from the surface under application of a sufficient electric field. This electric field threshold for electron emission can be significantly improved by surface patterning.

The development of low dimensional structures (on the nanoscale) provides surfaces where the local electric field is enhanced by several orders of magnitude.

The observed field emission from the zinc oxide nanostructures of the invention make them useful for the applications discussed above. Accordingly, in another aspect, the present invention provides a field emission device component comprising zinc oxide nanostructures of the invention.

The following non-limiting examples are provided to illustrate the present invention and in no way limit the scope thereof.

EXAMPLES

Example 1

Zinc Oxide Nanostructure Formation on Selected Substrates

1×1 cm samples of glass, quartz and silicon (the substrates) were mechanically cleaned by spraying compressed air onto the surface, and then placed around the cathode in an arc discharge chamber. The anode was a 99.999% pure zinc anode and the cathode was either a water-cooled high purity graphite disc or a water-cooled high purity copper disc. The distance between the anode and the cathode was fixed at 5 mm. The arc discharge was carried out at an air pressure of 400 Torr. After discharge for 20 seconds at 50 A, a bulk quantity of zinc oxide material adhered to the surface of the cathode and the inner wall of the chamber. A thin layer of material was also deposited onto the substrates in the chamber.

Figure 3A:
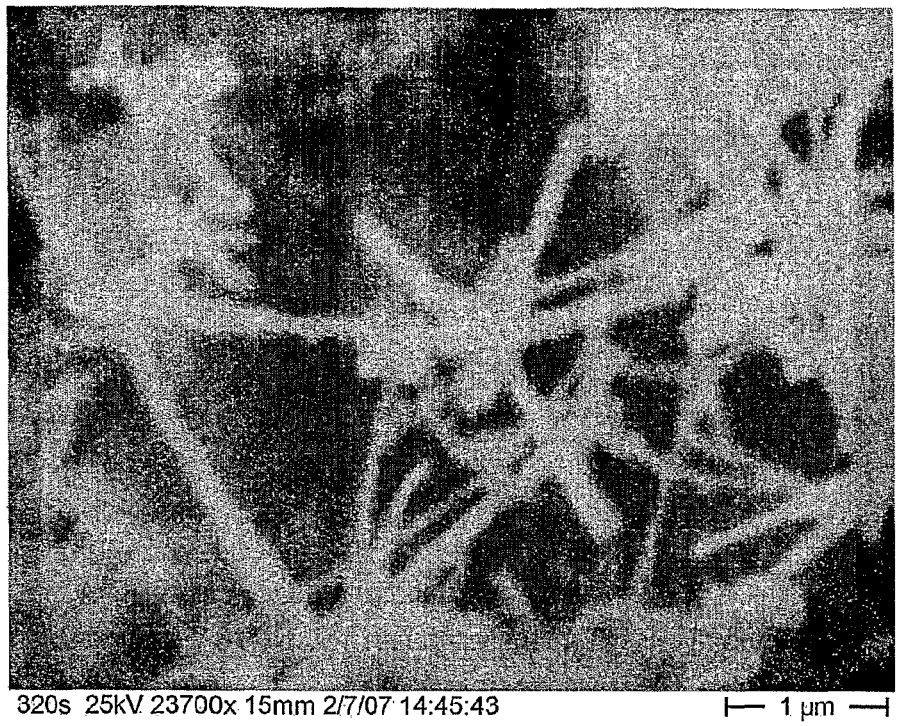
FIGS. 3(a) and 3(b) are scanning electron microscopy (SEM) images of zinc oxide nanorods formed on a substrate.
Figure 3B:
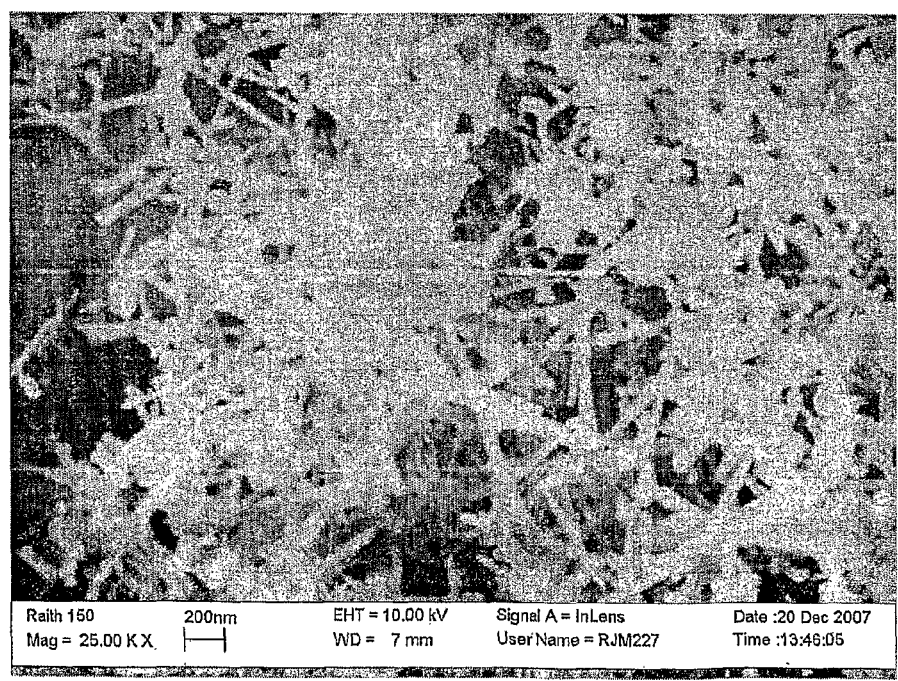

The morphology of the zinc oxide material was investigated by scanning electron microscopy (SEM). Typical SEM images of the zinc oxide material are shown in FIGS. 3(*a*) and 3(*b*), which show that the zinc oxide material predominantly comprises zinc oxide nanorods. The SEM images show closely packed rod-shaped structures with lengths of 0.1-5 µm and diameters of 20-400 nm.

Figure 4:
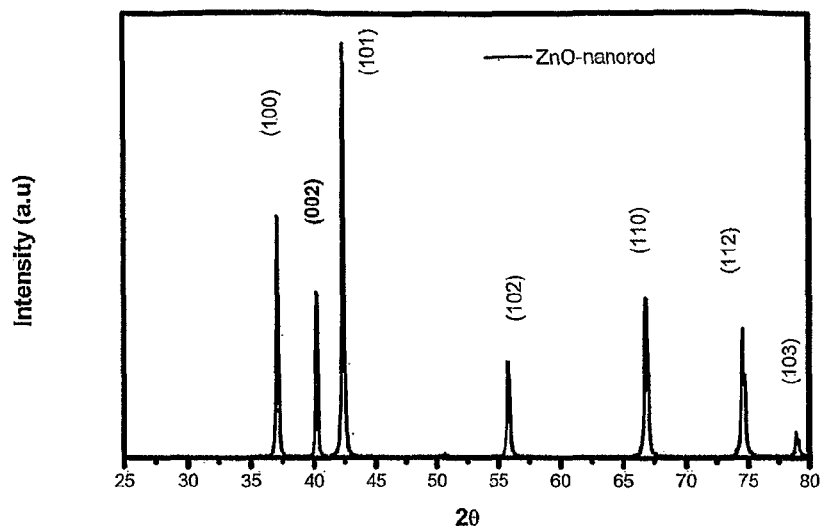
FIG. 4 is an X-ray diffraction (XRD) spectrum of zinc oxide nanorods produced in one embodiment.

The crystalline phase and preferred orientation of the zinc oxide nanorods was analysed by X-ray diffraction (XRD). The XRD spectrum is plotted in FIG. 4. The peaks were equivalent to d-spacings of 0.2814, 0.2603, 0.2476, 0.1911, 0.1625, 0.1477 and 0.1302 nm corresponding to (100), (002), (101), (102), (110), (112) and (103) plane reflections from hexagonal type zinc oxide with a=0.32498 nm and c=0.52066 nm. XRD revealed that the zinc oxide nanorods are high quality and singly crystalline. No diffraction peaks from any impurities were detected.

Figure 5:
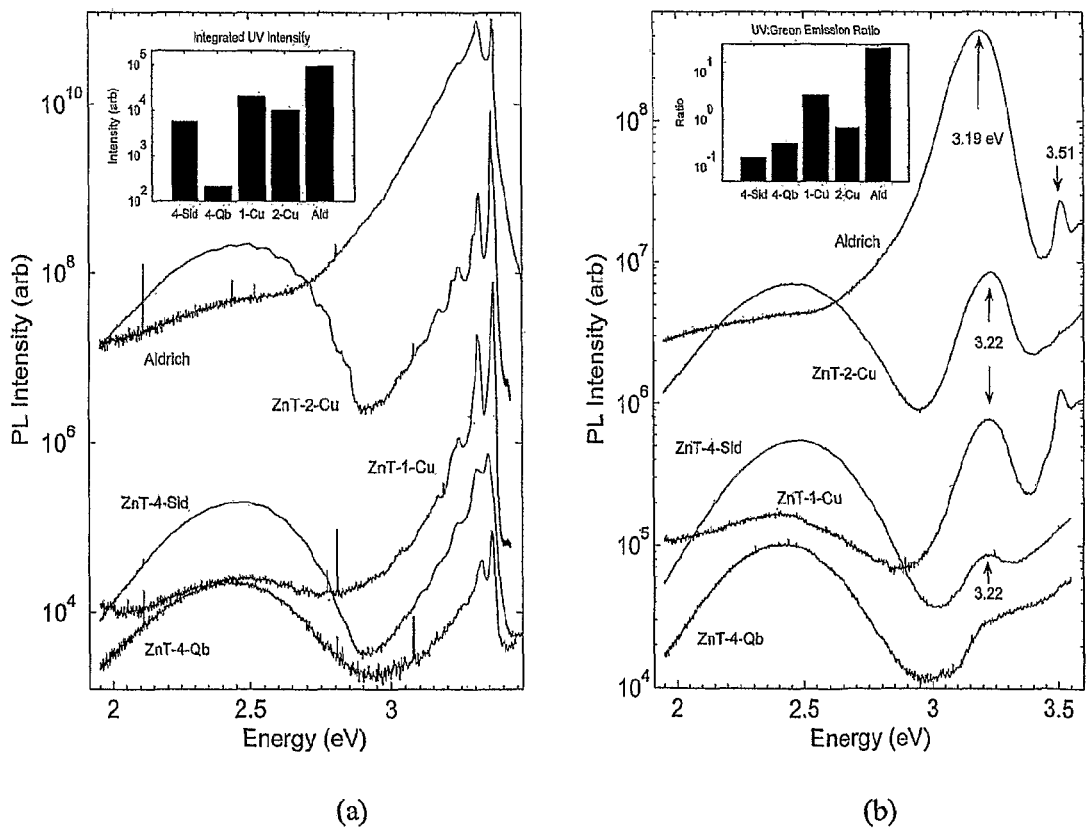
FIGS. 5(a) and 5(b) are photoluminescence (PL) spectra, at room temperature and low temperature, of zinc oxide nanorods formed on a substrate.

The optical properties of the zinc oxide nanorods were investigated using photoluminescence (PL) at room temperature and at 4 K. The PL spectra of zinc oxide nanorods prepared on silicon (ZnT-4-Sid) and quartz (ZnT-4-Qb) substrates along with two samples collected from the water-cooled copper cathode disc (ZnT-1-Cu and ZnT-2-Cu) and commercially available ZnO powder obtained from the Aldrich Chemical Company (Aldrich) at room temperature are plotted in FIG. 5(*a*) and at 4 K in FIG. 5(*b*).

The observed low temperature PL spectra are characteristic of ZnO emission at low temperature from the loose powder samples showing clearly excitonic, showing high intensities and narrow line widths. Violet emission was observed from all of the samples and originates either from donor-acceptor-pair transitions or surface states. Defect level emission in the green band from oxygen vacancies was observed from the arc discharge samples and showed Cu-related LO-phonon modulation.

At room temperature, the PL signals were strong, showing UV and green emission bands. The UV emission is likely from the A free excitonic peak. The Aldrich sample did not show significant green emission. PL from the arc discharge samples was usually, dominant, except for sample ZnT-1-Cu. This sample had a high UV to green integrated emission ratio implying the best structural quality and least defects. A high energy peak at 3.51 eV was observed for the Aldrich sample and sample ZnT-1-Cu but no previous reports of an emission at this energy have been published.

Example 2

Zinc Oxide Nanostructure Formation Under Different Oxygen Partial Pressures

Gas mixtures with different oxygen partial pressures were introduced into the arc discharge chamber. The gas mixtures were: 25% oxygen/75% argon; 50% oxygen/50% argon; and 99.5% $O_2$. The anode was a 99.999% pure zinc anode and the cathode was a water-cooled high purity graphite disc. The distance between the anode and the cathode was fixed at 5 mm. The total pressure was maintained at 500 Torr. After discharge for 20 seconds at 50 A, a bulk quantity of white material adhered to the surface of the graphite cathode and the inner wall of the chamber. This material was collected from the arc discharge chamber for further analysis.

The morphology of the zinc oxide material formed under different oxygen partial pressures was investigated by scanning electron microscopy (SEM). The SEM images showed that the zinc oxide material predominantly comprises zinc oxide nanorods. The morphology, especially at the top, and the length of the nanorods was observed to depend on the oxygen partial pressure.

Higher oxygen partial pressure during arc discharge resulted in the formation of nanorods having a higher aspect ratio. When the oxygen partial pressure was as high as 99%, the nanorods were tapered at the top and had lengths in the range of 0.02-10 µm. At lower oxygen partial pressures during arc discharge, the top of the nanorods became blunt and their length was reduced. The length of nanorods decreased from a range of 0.03-0.6 μm at an oxygen partial pressure of 50% to a range of 0.02-0.2 μm at an oxygen partial pressure of 25%.

Example 3

Formation of Ni-Doped Zinc Oxide Nanostructures

The arc discharge chamber was equipped with a rod formed from zinc (99.999% pure) doped with 1.8 wt % nickel (99.6% pure) as the anode. The cathode was a water-cooled high purity graphite disc. The distance between the anode and the cathode was fixed at 5 mm. The arc discharge was carried out at an air pressure of 500 Torr. After discharge for 20 seconds at 50 A, a bulk quantity of material adhered to the surface of the cathode and the inner wall of the chamber. This material was collected from the arc discharge chamber for further analysis.

Example 4

Sensors Comprising Zinc Oxide Nanorods

A glass substrate was cleaned in a sonicating bath of ethanol for about 30 minutes. The substrate was then coated with a gold thin film with thickness of about 100 nm using a gold sputter unit. A gap of about 1 mm was made on the surface of glass substrate.

BASF LUVISKOL® VA 64 (a nonionic polymeric film-forming agent) was mixed with zinc oxide nanorods prepared according to Example 1 and ethanol. The weight ratio of zinc oxide nanorods, BASF LUVISKOL® VA 64 and ethanol was kept at 3:1:8. For comparison, a sensor comprising zinc oxide nanorods was prepared without BASF LUVISKOL® VA 64, with a weight ratio of 2:1 for the zinc oxide nanorods and ethanol.

The zinc oxide nanorod mixture was ultrasonicated and then used to form a thinned layer on the substrate, by dropping the mixture onto the surface of the substrate and drying in the open air to evaporate the ethanol.

The amount of ethanol was adjusted to vary the final layer thickness of the layer of zinc oxide nanorods on the selected substrate. Thicknesses from about 100 nm to about 5 μm were obtained.

Two ends of the resulting film of zinc oxide nanorods were fixed via conductive silver paste on the gold-coated glass substrate. After annealing in air at 200° C. for 30 min, the silver paste formed solid conductive silver electrodes and a sensor comprising zinc oxide nanorods was obtained. After the sensor had cooled to room temperature, a light or dark gray material film was observed on the surface of the substrate. A schematic diagram of the sensor is shown in FIG. 2.

Figure 6:
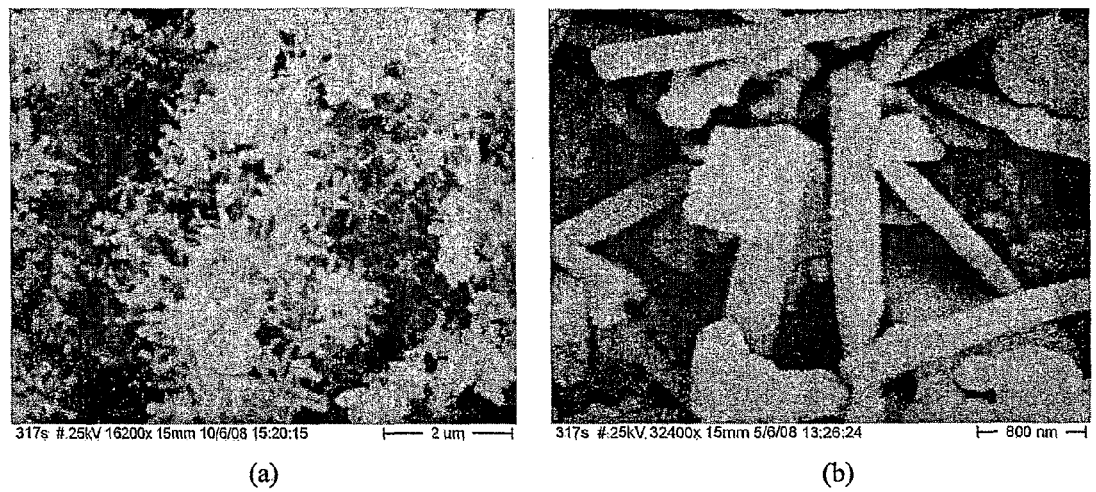
FIGS. 6(a) and 6(b) are SEM images of zinc oxide nanorods produced by arc discharge before and after ultrasonication.

FIG. 6 shows the SEM images of zinc oxide nanorods formed by arc discharge according to Example 1. The SEM image in FIG. 6(a) shows that the as-prepared product comprises closely packed rod-shaped structures with lengths of 0.1-5 μm and diameters of 20-400 nm. FIG. 6(a) shows that the as-prepared product comprises high quality zinc oxide nanorods with high purity. These nanorods, intersect to form 3D networks, which provide excellent structures for scattering water molecules and behaving as a porous film. The huge surface area makes the material suitable for sensor applications. After 30 minutes ultrasonication in ethanol with BASF LUVISKOL® VA 64, the nanorods separate as shown in FIG. 6(b).

The sensors were tested, using a standard electrical connection, under UV illumination and also under varying relative humidity. The sensors were connected to a variable voltage source with maximum compliance current set to 10 μA.

Photoresponsivity of Sensors Comprising Zinc Oxide Nanorods

Photoresponse measurements were carried out under illumination in the range of 310-470 nm with different wavelength UV LED diodes (from Seoul Optodevice Com.) at room temperature.

Figure 7:
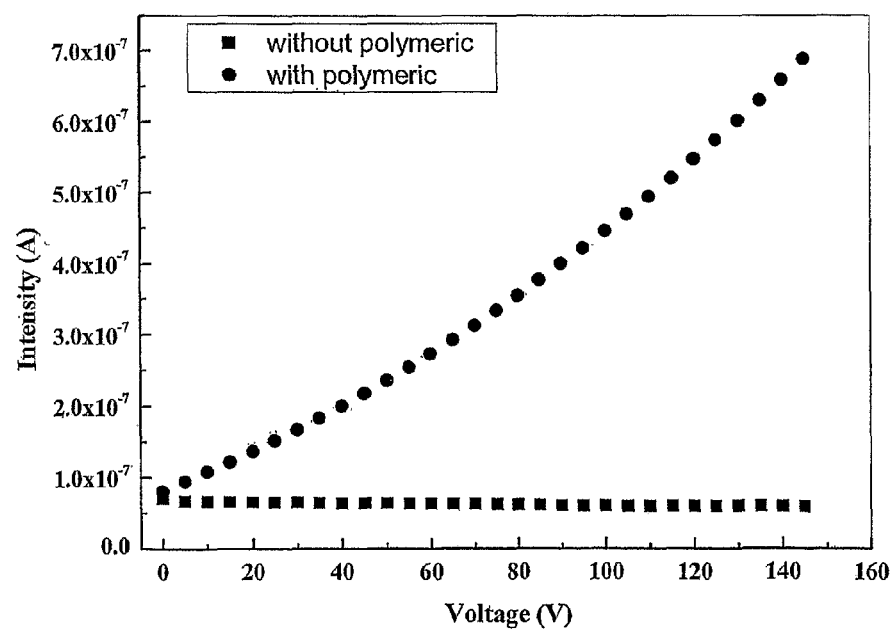
FIG. 7 shows the I-V curves, under 340 nm illumination, for sensors formed from zinc oxide nanorods with and without the addition of BASF LUVISKOL® VA 64.

FIG. 7 shows the IN curves under 340 nm illumination for sensors formed from zinc oxide nanorods with and without BASF LUVISKOL® VA 64 (a nonionic polymeric film-forming agent) in the precursor ethanol/zinc oxide nanorod mixture. The conductivity of the sensor improved when BASF LUVISKOL® VA 64 was used. The intensity for the sensor increased by more than an order of magnitude from $6.41 \times 10^{-8}$ to $2.36 \times 10^{-7}$ when the bias was set as 50 V, which corresponds to the decrease of the resistance of the sensor.

Sensors formed from zinc oxide nanorods with BASF LUVISKOL® VA 64 were used in the subsequent tests.

Figure 8A:
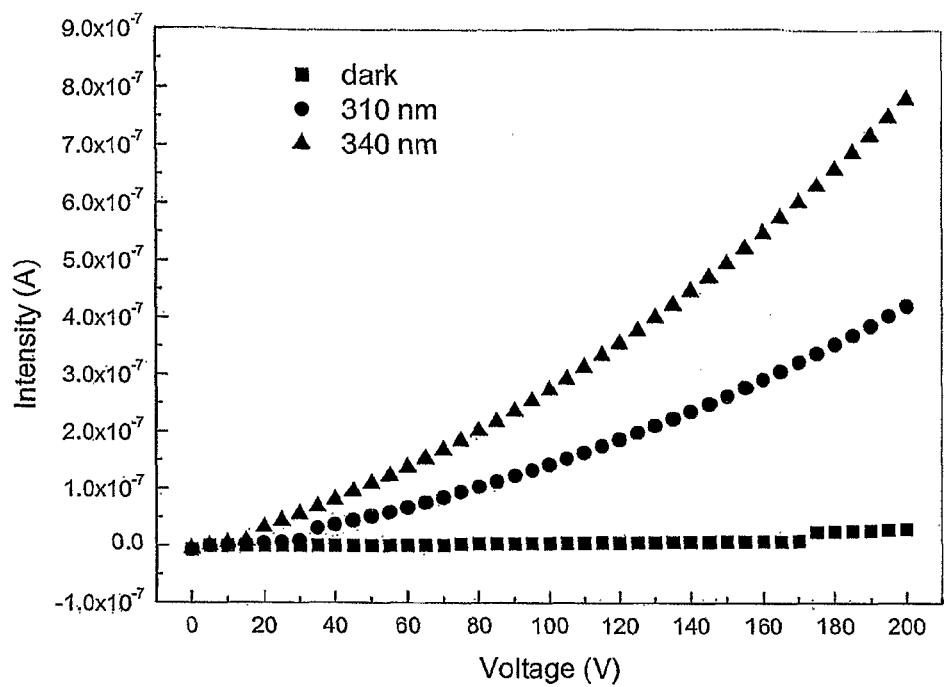
FIG. 8(a) is the I-V curve, in the dark and under illumination with different wavelengths, of a sensor comprising zinc oxide nanorods before annealing.
Figure 8B:
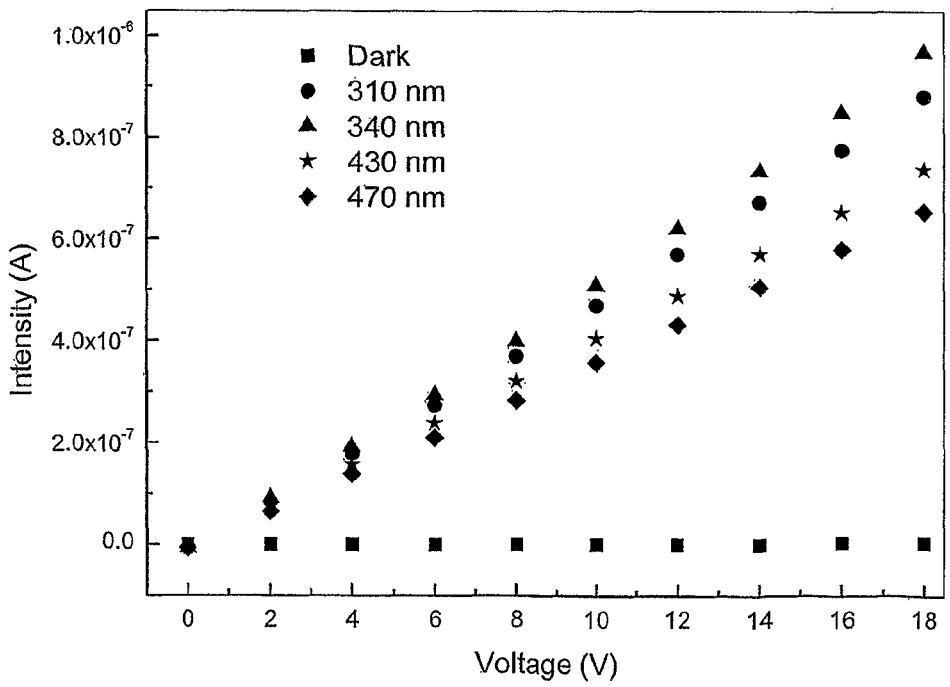
FIG. 8(b) is the I-V curve, in the dark and under illumination with different wavelengths, of a sensor comprising zinc oxide nanorods after annealing.

FIG. 8 show typical I-V characteristics of a zinc oxide nanorod sensor measured in the dark and under different illumination before (FIG. 8(a)) and after (FIG. 8(b)) annealing in air. The zinc oxide nanorod film is very resistive in the dark, which is desirable for good sensor. The photocurrent increased by 3 orders of magnitude from $5.51 \times 10^{-11}$ A to $3.27 \times 10^{-8}$ A at 18 V for the sensor without annealing. After annealing in air, the sensor exhibited a current increase of nearly 4 orders of magnitude from $2.7 \times 10^{-10}$ A to $1.0 \times 10^{-6}$ A at 18 V under UV illumination 340 nm. These results indicate UV-sensitive photoconduction in the zinc oxide nanorod sensors. The improved photoconductivity after annealing demonstrated that annealing in air at 200° C. formed good ohmic contacts to the zinc oxide nanorod film, which contributes to the increase of the conductivity of the device.

The sensors used in the subsequent tests were annealed.

Figure 9:
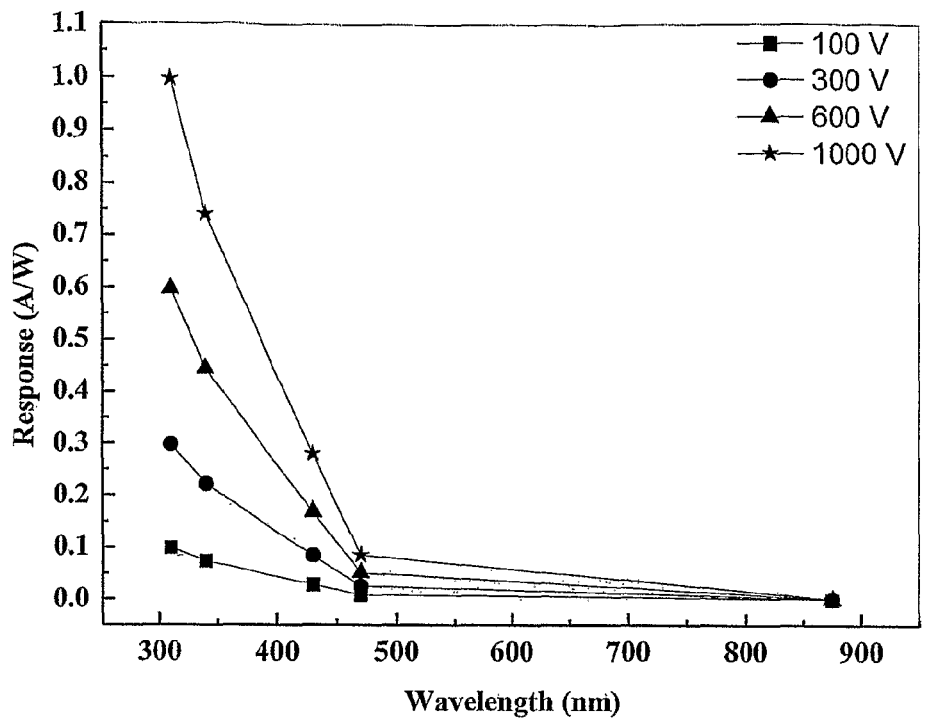
FIG. 9 depicts the dependency of responsivity, under illumination at different wavelengths, on biased voltage for a sensor comprising zinc oxide nanorods.

FIG. 9 shows the dependency of responsivity for the zinc oxide nanorod sensor on biased voltage under different wavelengths of illumination. The internal photocurrent gain in the sensor is not very high. The zinc oxide nanorod sensor exhibited a responsivity of about 0.01 to 1.0 A/W under UV (340 nm) illumination.

Figure 10:
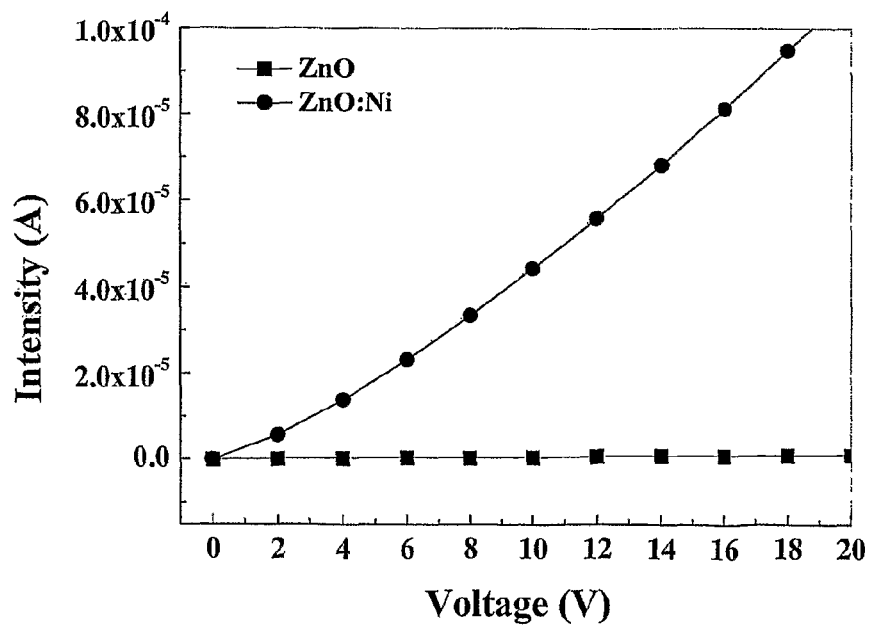
FIG. 10 shows the I-V curve, under 340 nm illumination, for sensors formed from zinc oxide nanorods and from nickel-doped zinc oxide nanorods.

FIG. 10 shows the 1-V curves under 340 nm illumination for sensors formed from zinc oxide nanorods prepared according to Example 1 and nickel-doped zinc oxide nanorods prepared according to Example 3. Both sensors showed a UV-sensitive photoconduction when the bias increased from 0 V to 18 V. The intensity for the sensor using nickel-doped zinc oxide nanorods increased by nearly four orders of magnitude from $5.21 \times 10^{-9}$ to $9.48 \times 10^{-5}$. The intensity for the sensor using undoped zinc oxide nanorods increased by about two orders of magnitude.

Humidity Measurement

A zinc oxide nanorod sensor was placed in a dark box with a fog generator that enabled the relative humidity (RH) to be varied from 7% to 95% RH at an ambient temperature of 25° C. The RH levels were independently monitored using a standard hygrometer. A computer-controlled Keithley semiconductor analyzer was used to measure the change of the sensor's resistance in the testing circuit.

Figure 11:
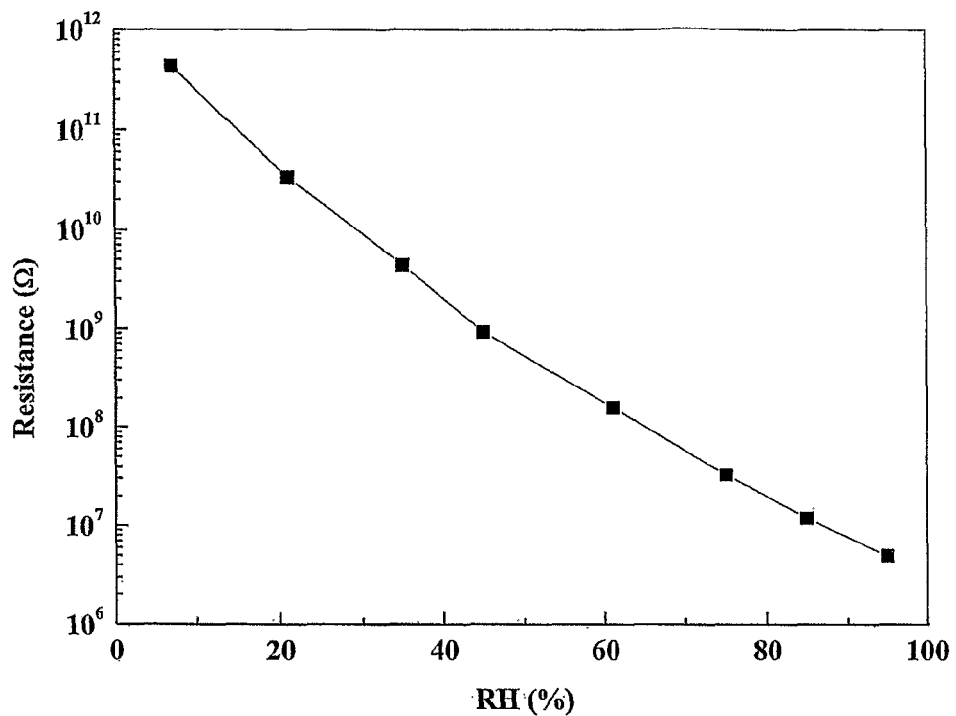
FIG. 11 depicts the dependency of resistance on relative humidity at 25° C. for a sensor comprising zinc oxide nanorods.

FIG. 11 is a plot of resistance as, a function of RH at 25° C. The resistance of the sensor decreased almost linearly with increasing relative humidity. The resistance was about 4.35×

$10^{11}$ in dry air (7% RH) and decreased to about $4.95 \times 10^6$ in 95% RH air. Therefore, the resistance decreased by approximately five orders of magnitude ($10^{11}$-$10^6$) over the RH range of 7-95% RH, showing very high sensitivity and good linearity.

The sensitivity factor $S_f$ was calculated as $S_f = R_{7\%}/R_{95\%} = 8790$.

Figure 12:
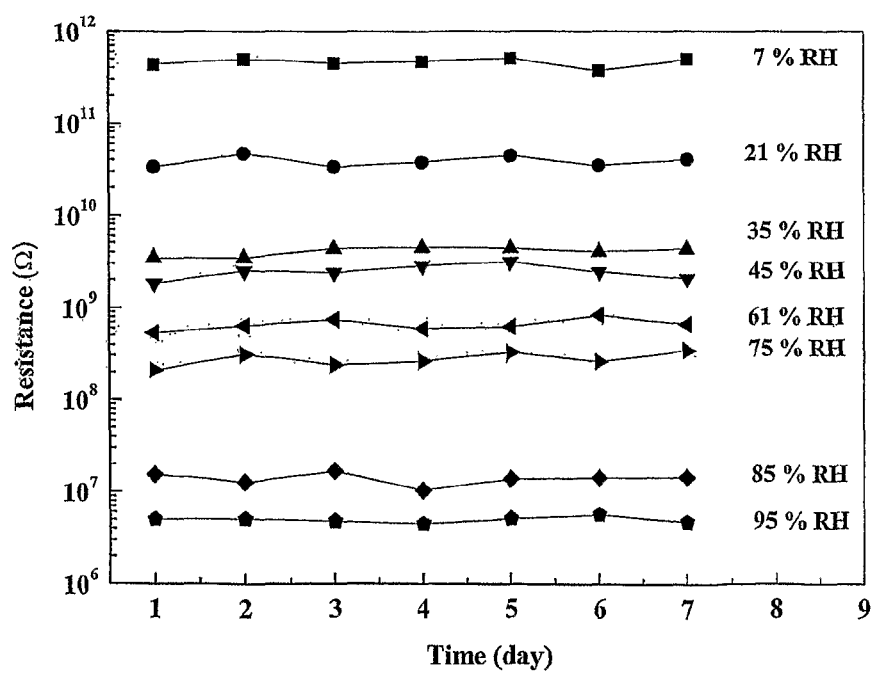
FIG. 12 depicts the variation of resistance with time at different relative humidity levels for a sensor comprising zinc oxide nanorods.

The sensor's stability was tested by exposing it to air for 1 week, followed by measuring resistance at various RH levels. A plot of the variation of resistance with time at different relative humidity levels is shown in FIG. 12. A slight variation in resistance shift is observed over this time, which directly confirms the sensor's stability and indicates that the sensor is suitable for use as a practical humidity sensor.

These results indicate that the resistance of the zinc oxide nanorod film is strongly affected by water vapour in air, and that the resistance change resulting from the fluctuation of RH in air is reversible. Water-related conduction in ceramic and porous materials mainly occurs as a surface mechanism. The resistance change of the zinc oxide nanorod film with increased RH may also relate to the adsorption of water molecules on the surface of the nanorods. As the RH increases so does the number of water molecules available to adsorb to the surface of the nanorods. Generally, water molecules act as a donor, contributing electrons to oxide semiconductor materials. Without wishing to be bound by theory, it is thought that the surface structure of the zinc oxide nanorods enables them to absorb moisture easily on their porous surface, which contributes to the decrease in resistance with increased RH.

Electrical Properties of Zinc Oxide Nanorods

The electrical properties of a thin film of zinc oxide nanorods on a glass substrate were measured using the Hall probe technique. The nanorods are n-type having typical carrier concentrations from $-1.0 \times 10^{11}$-$5.0 \times 10^{13}$ cm$^{-3}$, hole mobilities from 10-700 cm$^2$vs$^{-1}$ and resistivities from $1 \times 10^3$-$1 \times 10^{10}$ ohm cm.

Field Emission from Zinc Oxide Nanorods

Figure 13:
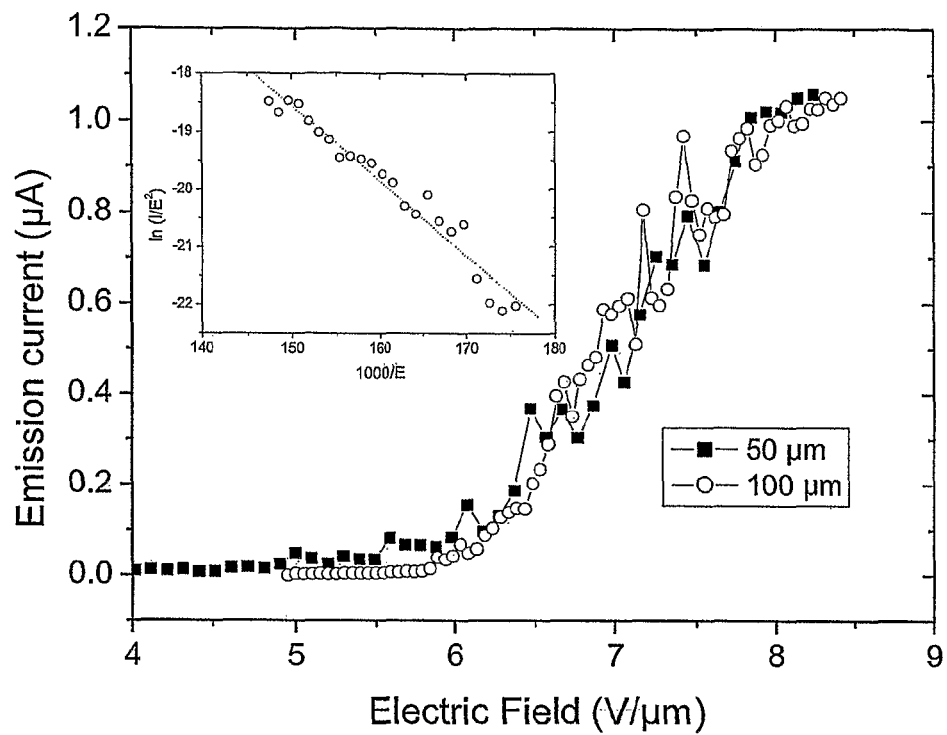
FIG. 13 is a plot of the field emission current against electric field for zinc oxide nanorods formed in one embodiment.

The zinc oxide nanorods were mounted onto a metallic substrate using silver conductive paste and electrically connected to a stainless steel block. The zinc oxide nanorods were the cathode material and were placed in a vacuum system at $10^{-7}$ mbar. The anode was a highly polished stainless steel rod with a circular flat tip of 4 mm diameter. The anode was mounted on a micro-adjustment system (2 μm resolution) to set the anode-cathode separation. A DC voltage was applied, and current measured, between the cathode and anode using a Keighley 237 source measure unit. The emission current was measured as a function of anode-cathode separation. FIG. 13 shows the field emission current measured against electric field for separations of 50 and 100 μm. The turn-on field, which is defined as 1 μA/cm$^2$, was typically in the range 3-10 V/μm.

Figure 14:
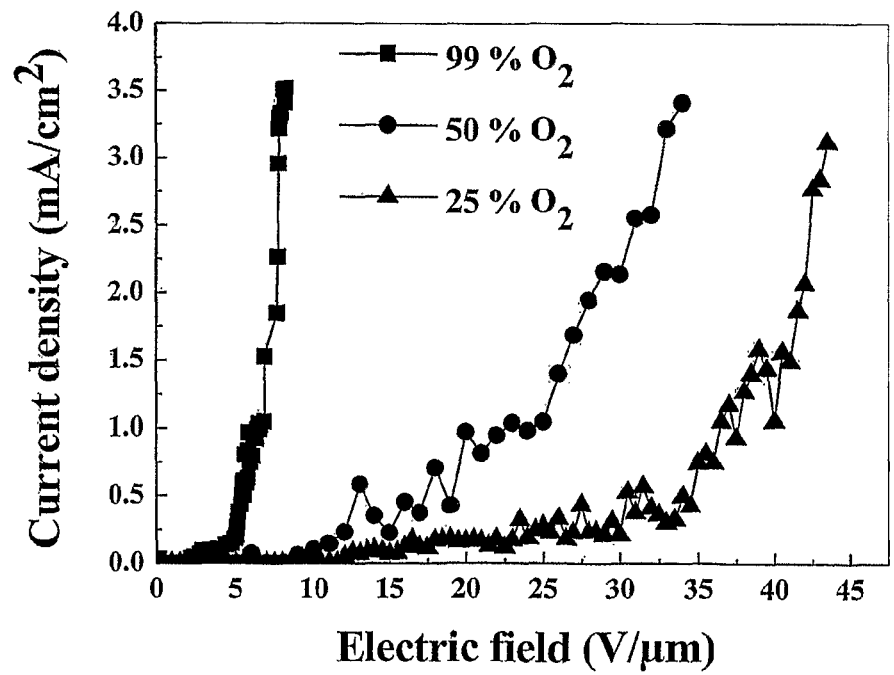
FIG. 14 is a plot of the field emission current against electric field for zinc oxide nanorods formed under different oxygen partial pressures.

FIG. 14 shows the field emission current density as a function of the applied electric field for zinc oxide nanorods formed under different oxygen partial pressures according to Example 2. The zinc oxide nanorods formed under 99.5% oxygen partial pressure showed a turn-on electric field of 3 V/μm at a current density of 10 μA/cm$^2$ and an emission current density of 1 mA/cm$^2$ under the threshold field of 6.6 V/μm.

Table 1 lists the turn-on field, threshold field and enhancement factor for zinc oxide nanorods formed under different oxygen partial pressures.

TABLE 1

| O$_2$ partial pressure | Turn-on field (V/μm) | Threshold field (V/μm) | Field enhancement factor (β) |
| --- | --- | --- | --- |
| 99.5% | 3 | 6.6 | 4790 |
| 50% | 7.8 | 22.1 | 1940 |
| 25% | 11.5 | 36.5 | 580 |

It is not the intention to limit the scope of the invention to the above-mentioned examples only. As would be appreciated by a skilled person in the art, many variations are possible without departing from the scope of the invention as set out in the accompanying claims.

The invention claimed is:

1. A method for producing zinc oxide nanostructures, the method comprising:
   providing a zinc anode and a cathode in an arc discharge chamber, wherein the cathode is arranged horizontally in the arc discharge chamber and the anode is arranged vertically and above the cathode;
   supplying current to the anode and the cathode to establish an arc discharge between the cathode and the anode to vaporise the anode and produce the zinc oxide nanostructures;
   terminating the current supply to the anode and the cathode; and
   collecting the resulting zinc oxide nanostructures.

2. A method as claimed in claim 1, wherein the zinc anode is at least 99.0% pure, at least 99.9% pure, at least 99.99% pure, or at least 99.999% pure.

3. A method as claimed in claim 1, wherein the anode comprises zinc doped with one or more metallic donor.

4. A method as claimed in claim 3, wherein the one or more metallic donor comprises from about 0.1 atomic % to about 10 atomic % of the anode.

5. A method as claimed in claim 3 wherein the metallic donor is nickel.

6. A method as claimed in claim 1, wherein the pressure in the arc discharge chamber is selected from the group consisting of about 300 Torr (40 kPa) to about 700 Torr (93.3 kPa); about 400 Torr (53.3 kPa), and about 500 Torr (66.7 kPa).

7. A method as claimed in claim 1, wherein the atmosphere in the arc discharge chamber is selected from the group consisting of at least about 10% oxygen, about 21% oxygen, about 25% oxygen, about 50% oxygen, and about 99.5% oxygen.

8. A method as claimed in claim 1, wherein the atmosphere in the arc discharge chamber comprises a mixture of oxygen and argon.

9. A method as claimed in claim 1, wherein the atmosphere in the arc discharge chamber comprises air.

10. A method as claimed in claim 1, wherein the current supplied to the anode and the cathode is between about 30 A and about 70 A, or is about 50 A.

11. A method as claimed in claim 1, wherein the arc discharge between the cathode and the anode is established for between about 10 seconds and about 50 seconds, or for about 20 seconds.

12. A method as claimed in claim 1 further comprising placing a nanostructure growth substrate in the arc discharge chamber before establishing the arc discharge between the cathode and the anode.

13. A method as claimed in claim 12, wherein the nanostructure growth substrate is selected from the group consisting of: silicon; glass; and quartz.

14. A method as claimed in claim 12, wherein the nanostructure growth substrate is substantially planar.

15. A method as claimed in claim 1, wherein the zinc oxide nanostructures are nanorods.

16. A method as claimed in claim 15, wherein the nanorods have a diameter between about 20 nm and about 400 nm and a length between about 0.02 μm and about 10 μm.

17. A method for producing a sensor component comprising the steps of:
- providing a zinc anode and a cathode in an arc discharge chamber, wherein the cathode is arranged horizontally in the arc discharge chamber and the anode is arranged vertically and above the cathode;
- supplying current to the anode and the cathode to establish an arc discharge between the cathode and the anode to vaporise the anode and produce the zinc oxide nanostructures;
- terminating the current supply to the anode and the cathode;
- collecting the resulting zinc oxide nanostructures;
- providing a sensor substrate comprising a conducting thin film at least partially covering at least two regions on at least one surface of a sensor substrate material to define a gap in the conducting thin film; and then
- applying a mixture comprising the zinc oxide nanostructures and a nonionic polymer to at least a portion of the gap in the conducting thin film and thereby bridge the gap to provide the sensor component.

18. A method as set forth in claim 17 further comprising the step of annealing the mixture of zinc oxide nanostructures and nonionic polymer applied to the sensor substrate.

* * * * *